(12) United States Patent
Reimann et al.

(10) Patent No.: US 7,541,395 B2
(45) Date of Patent: Jun. 2, 2009

(54) TWO-STEP MIXING PROCESS FOR PRODUCING AN ABSORBENT POLYMER

(75) Inventors: Armin Reimann, Willich (DE); Manfred Van Stiphoudt, Kempen (DE); Herbert Vorholt, Haltern (DE)

(73) Assignee: Evonik Stockhausen GmbH, Krefeld (DE)

( * ) Notice: Subject to any disclaimer, the term of this patent is extended or adjusted under 35 U.S.C. 154(b) by 448 days.

(21) Appl. No.: 10/532,401

(22) PCT Filed: Oct. 24, 2003

(86) PCT No.: PCT/EP03/11830

§ 371 (c)(1), (2), (4) Date: Aug. 19, 2005

(87) PCT Pub. No.: WO2004/037900

PCT Pub. Date: May 6, 2004

(65) Prior Publication Data

US 2006/0057389 A1   Mar. 16, 2006

(30) Foreign Application Priority Data

Oct. 25, 2002   (DE) ................................. 102 49 822

(51) Int. Cl.
*B32B 9/04* (2006.01)
*C08F 118/02* (2006.01)
*B01F 3/08* (2006.01)

(52) U.S. Cl. ..................... 523/346; 526/319; 428/411.1

(58) Field of Classification Search ................. 526/319; 523/346; 428/411.1
See application file for complete search history.

(56) References Cited

U.S. PATENT DOCUMENTS 4,703,132 A   10/1987   Marciano-Agostinelli et al.

(Continued)

FOREIGN PATENT DOCUMENTS

DE   68916707 T2   3/1995

(Continued)

OTHER PUBLICATIONS

International Preliminary Examination Report completed on Jan. 12, 2005 in connection with PCT/EP2003/011830.

(Continued)

*Primary Examiner*—Ling-Siu Choi
*Assistant Examiner*—Michael M Bernshteyn
(74) *Attorney, Agent, or Firm*—Smith Moore Leatherwood LLP

(57) ABSTRACT

A process for producing an absorbent polymer including a first mixing event, in which a plurality of absorbent polymer particles (1) are mixed with a liquid (2) and a second mixing event, in which the liquid (2) is homogenized within the interior of the polymer particles. The polymer particles (1) in the first mixing event are mixed with a speed such that the kinetic energy of the individual polymer particles (1) is on average larger than the adhesion energy of the individual polymer particles (1), and the polymer particles (1) in the second mixing event are stirred at a lower speed than in the first mixing event. The different speeds effect a fluidization of the polymer particles (1), which prevents a clumping of the polymer particles (1) during the mixing event. The absorbent polymers thus produced are distinguished by a particularly rapid swelling behavior.

14 Claims, 3 Drawing Sheets

U.S. PATENT DOCUMENTS

| | | |
|---|---|---|
| 4,818,534 A | 4/1989 | Levy |
| 4,983,389 A | 1/1991 | Levy |
| 4,983,390 A | 1/1991 | Levy |
| 4,985,251 A | 1/1991 | Levy |
| 5,002,986 A * | 3/1991 | Fujiura et al. ............... 524/47 |
| 5,124,416 A | 6/1992 | Haruna et al. |
| 5,567,430 A | 10/1996 | Levy |
| 5,824,328 A | 10/1998 | Levy |
| 5,837,789 A | 11/1998 | Stockhausen et al. |
| 6,056,854 A | 5/2000 | Woodrum |
| 6,060,557 A | 5/2000 | Dahmen et al. |
| 6,071,976 A | 6/2000 | Dairoku et al. |
| 6,323,252 B1 * | 11/2001 | Gartner et al. ............. 521/149 |
| 6,350,710 B1 | 2/2002 | Jonas et al. |
| 6,403,700 B1 | 6/2002 | Dahmen et al. |
| 6,410,610 B1 | 6/2002 | Brehm |
| 6,414,214 B1 | 7/2002 | Engelhardt et al. |
| 6,562,879 B1 | 5/2003 | Hatsuda et al. |
| 6,605,673 B1 | 8/2003 | Mertens et al. |
| 6,620,889 B1 | 9/2003 | Mertens et al. |
| 2002/0031635 A1 | 3/2002 | Jonas et al. |
| 2003/0207997 A1 | 11/2003 | Mertens et al. |
| 2005/0074614 A1 | 4/2005 | Jonas et al. |

FOREIGN PATENT DOCUMENTS

| | | |
|---|---|---|
| DE | 19529348 C2 | 2/1997 |
| DE | 19646484 A1 | 5/1997 |
| DE | 68927913 T2 | 7/1997 |
| DE | 19645240 A1 | 1/1998 |
| DE | 19813443 A1 | 10/1998 |
| DE | 19748153 A1 | 5/1999 |
| DE | 19909653 A1 | 9/2000 |
| DE | 19909838 A1 | 9/2000 |
| DE | 19941072 A1 | 3/2001 |
| DE | 19941423 A1 | 3/2001 |
| DE | 10052966 A1 | 5/2002 |
| JP | 9124879 | 5/1997 |
| JP | 9235378 | 9/1997 |
| JP | 2000302876 | 10/2000 |
| JP | 2003511489 T | 3/2003 |
| WO | WO 98/49221 | 11/1998 |

OTHER PUBLICATIONS

Edana, Moisture Content, test method, Feb. 1999, pp. 1-6, 430.1-99, Edana.

Edana, Centrifuge Retention Capacity, test method, Feb. 1999, pp. 1-5, 441.1-99, Edana.

Edana, Absorbency Against Pressure, test method, Feb. 1999, pp. 1-7, 442.1-99, Edana.

* cited by examiner

TWO-STEP MIXING PROCESS FOR PRODUCING AN ABSORBENT POLYMER

This application is a national stage application under 35 U.S.C. 371 of international application no. PCT/EP2003/011830 filed Oct. 24, 2003, which is based on German Application No. DE 102 49 822.9, filed Oct. 25, 2002, and claims priority thereto.

BACKGROUND OF THE INVENTION

The invention is related to a process for producing an absorbent polymer, an absorbent polymer obtainable by this process, an absorbent polymer, a composite, a process for producing the composite, a composite obtainable by this process, chemical products as well as the use of the absorbent polymer and of the composite.

In order to form so-called "superabsorbent" polymers a polymerization of different types of normally water-soluble monomers, often however also of water insoluble co-monomers, together with the presence of cross-linkers, is necessary. The addition of the cross-linkers occurs during or after the polymerization. Superabsorbent polymers of this type are lightly cross-linked, water insoluble hydrogel polymers, which have a large capacity for water absorption in the dry and in the essentially water-free state. The absorbed quantities of water can constitute a multiple of the weight of the superabsorbent polymer itself.

Because of this high absorption capacity superabsorbent polymers are suitable for water absorbent structures and objects, such as for example baby diapers, incontinence products or sanitary napkins.

Although the ratio of the absorbed weight of water to the dry weight of the polymer, i.e. the absorption capacity, is sufficient for applications of this type, the rate with which the water is absorbed, i.e. the rate of absorption, is limited and for many application cases unsatisfactory. In many cases the high absorption capacity of the superabsorbent polymers has no effect, since the slow absorption rate prevents a sufficiently fast absorption of the water and thereby renders difficult the use of the polymers in hygiene applications.

WO-A-98/49221 describes a process for improving the properties of absorbent polymer particles, in which the polymer particles which, for example during a secondary cross-linking reaction, have been heated beforehand for at least 10 minutes at least 170° C., are mixed with an aqueous additive solution. Upon mixing the polymers with an aqueous solution, however, agglomeration of the polymer particles occurs, which according to the teaching of WO-A-98/49221 can only be prevented by addition of additives to the aqueous solution, for example in the form of singly or multiply charged metal cations.

In general the object of the present invention is to overcome the disadvantages arising from the state of the art.

It is in particular an object of the present invention to specify a process by which the superabsorbent polymers can be produced, which polymers have an increased rate of absorption towards water without appreciably reducing their absorption capacity. In addition this process should be carried out in a simple way and be possible without the use of additives, in particular without the use of organic additives.

A further object of the invention consists especially in providing a superabsorbent polymer, composites which comprise superabsorbent polymers of this type and chemical products which comprise superabsorbent polymers or composites of these types, wherein the superabsorbent polymer has an increased rate of absorption towards water. In addition the absorption properties of these polymers under mechanical load, which occur in particular upon transport of the polymer particles in conveyor systems, should not be negatively influenced. In particular the absorption capacity of the polymer under a force load due to mechanical load should not be decreased at all if possible or at least be only slightly reduced (=mechanical stability).

BRIEF DESCRIPTION OF THE DRAWINGS

The present invention is better understood by a reading of the Detailed Description of the Invention along with a review of the drawings in which.

DETAILED DESCRIPTION OF THE INVENTION

Figure 1:
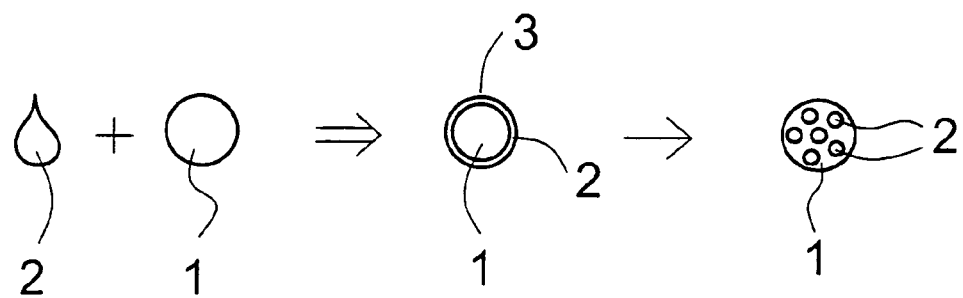
FIG. 1 illustrates both steps of the process according to the invention for producing an absorbent polymer.

These objects are achieved by the objects of the category-forming claims. Advantageous embodiments and further forms which can occur individually or in combination are the object of the respective independent claims.

In the process according to the invention for producing an absorbent polymer, comprising a first mixing event, in which a plurality of absorbent polymer particles are mixed with a liquid, and a second mixing event, in which the liquid is distributed, preferably homogenized, within the polymer particles, the polymer particles are mixed in the first mixing event at a speed such that the kinetic energy of the individual polymer particles is on average greater than the adhesion energy between the individual polymer particles, and the polymer particles in the second mixing event are stirred at a lower speed than in the first mixing event.

In the first mixing event the polymer particles are wetted at their surface with the liquid. The polymer particles are stirred in the first mixing event at a higher speed than in the second mixing event.

The high speed effects a fluidization of the polymer particles, which prevents the polymer particles from remaining adhered to each other and clumping. The high speed leads, in the case of an adhesion of two polymer particles to each other, to dissociation of both clumped polymer particles from each other through a collision with a third polymer particle or through collision of the clumped polymer particles with a wall e.g. of the mixer.

The condition that the kinetic energy of the individual polymer particles is on average larger than the adhesion energy between the individual polymer particles results in the polymer particles being found predominantly as individuals and not as composites, agglomerations or drops. Since the adhesion energy is smaller than the kinetic energy, the polymer particles are found in constant movement as individuals.

The liquid is equally distributed via the movement of the polymer particles and the numerous impacts with each other. The surfaces of the polymer particles are evenly wetted with liquid.

In the first mixing event large dynamic forces arise which are caused by the high speeds of the polymer particles. The quasi-static forces are however small in comparison.

By means of the second mixing event, the polymer particles mature in the manner that the liquid distributes itself within the polymer particles.

A clumping of the polymer particles or an agglomeration of the polymer particles is prevented by the low speed of the polymer particles in the second mixing event. Preferably the selected speed in the second mixing event is so small that the quasi-static compression force is kept low. As a result a clumping is impeded.

In one embodiment of the process according to the invention there is a maturation event between the first mixing event and the second mixing event, in which the polymer particles are moved against each other less than in the first and second mixing events. Preferably the polymer particles rest in the maturation event. The polymer particles preferably remain in the maturation event for a period of time from about 1 second to about 10 hours, preferably about 1.1 seconds to about 60 minutes and particularly preferably about 1.5 seconds to about 20 minutes.

In another embodiment of the process according to the invention the average speed of the polymer particles in the first mixing event amounts to between about 8 and about 80 m/sec, in particular about 10 and about 70 m/sec, above all preferably between about 15 and about 60 m/sec.

With such high average speeds in the first mixing event sufficiently large kinetic energies are reached for the typical densities of the absorbent polymer granulates or the weights of the individual polymer particles. These large kinetic energies act in opposition to the effort of the polymer particles to remain adhered together. The effort of the polymer particles to remain adhered together is characterized by the adhesion energy. The size of the adhesion energy depends upon a plurality of parameters, among others on the cohesion of the liquid, the adhesion between liquid and polymer particles as well as the cohesion between two (optionally partially swollen) polymer particles. The adhesion energy is essentially given by how much energy is necessary to separate from each other two adhered together polymer particles.

The second mixing event occurs with sufficiently small quasi-static forces. Large static forces result in a clumping of the polymer particles. In order to prevent high static forces appropriate mixer types such as e.g. screw mixers are used. Furthermore the second mixing event can occur in a drum which according to one embodiment has mixing paddles on the drum wall. Such mixer types are inexpensive and economical in use.

The level of the speeds in the first mixing event as well as the speeds in the second mixing event depend on the particular type of the absorbent polymer. The speeds can be determined by statistical considerations as well as by simple measurements. For example the minimum speed necessary for the first mixing process is determined from the average kinetic energy necessary to overcome the adhesion energy. The adhesion energy is the energy necessary to separate two clumped together polymer particles from each other. It can be determined by a measurement. Using these speeds for the respective mixing events has the effect that the polymer particles do not remain adhered to each other. If the polymer particles do not clump, the surface of the polymer granulates remains maximal, whereby a rapid absorption of water is effected.

In a further embodiment of the process according to the invention the average speed of the polymer particles in the second mixing event amounts to less than about 3 m/sec, particularly under about 0.3 m/sec, preferably under about 0.03 m/sec. These low speeds prevent an agglomeration of the polymer particles.

In a further embodiment of the process according to the invention for producing an absorbent polymer the Froude number in the first mixing process amounts to between about 1 and about 50, in particular between about 1.1 and about 45, further preferred between about 1.5 and about 40, particularly preferred between about 1.7 and about 33 and even more preferred between about 10 and about 33. In a particular embodiment of the process according to the invention the Froude number in the first mixing event amounts to at least about 5, preferred at least about 10, particularly preferred at least about 15, more preferred at least about 20 and above all even more preferred at least about 25, whereby preferably a value of about 60 is not exceeded. If too high Froude numbers or speeds are selected the polymer particles are disadvantageously altered.

The Froude number in the second mixing event amounts according to the invention to preferably between about 0.001 and about 1, in particular between about 0.01 and about 0.2, preferably between about 0.08 and about 0.03.

The Froude number is a characteristic characterizing number, which determines for rotation mixers the mixing effect of the mixer independently from the dimensions of the mixer. The Froude number $Fr=(R\times\omega^2)/g$ gives the centrifugal acceleration of the products to be mixed, normalized with respect to acceleration due to gravity, wherein R is the radius of the rotation mixer, $\omega$ the rotation frequency of the rotation mixer and g the gravitational constant ($=9.81$ m/s$^2$). By specifying the Froude number an apparatus-independent mixing effect can be specified independent of the individual set-up of the mixer by specifying a normalized acceleration.

The Froude number necessary for the fluidization in the first mixing event for typical superabsorbent polymers is, according to experience, reached between about 1.7 and about 33. For polymer particles, which have a lower density and thereby a lower mass, assuming that the adhesion energy is the same, correspondingly larger Froude numbers are to be applied. The lighter the polymer particles are, the higher their speeds must be, so that an adhesion or a clumping is broken up through the movement of the polymer particles. For heavier polymer particles correspondingly lower speeds or smaller Froude numbers are necessary.

The second mixing event demands lower speeds, which correspond to smaller Froude numbers. What is important in the second mixing event, is that only low static forces develop, which result in a clumping of the polymer particles.

In a particular embodiment of the process according to the invention the polymer particles are back-mixed in the first mixing event. Back-mixing means that older polymer particles, which have already been mixed for a while, are put together with polymer particles which are freshly wet with liquid. This happens preferably in a continual mixing process. In such a mixing process the flow of the new polymer particles entering the mixer is superposed by a flow of polymer particles already present in the mixer, counter to the entering flow. Preferably the ratio of the counter flow to the flow of the newly entering polymer particles, i.e. back-mixing, amounts to about 5% to about 50%, preferably about 10% to about 30% and particularly preferably about 15% to about 25%. The back-mixing is effected by a suitable configuration of the mixing organ (propeller) of the mixer. The back-mixing causes a particularly even wetting of the polymer particles with liquid to be achieved. A particularly even homogenization of the liquid within the polymer particles contributes to the polymer particles being characterized by fast liquid absorption.

In a special embodiment of the process the mean residence time of the first mixing event amounts to between about 5 and about 200 sec, in particular between about 10 and about 100 sec, preferably between about 20 and about 60 sec. By the mean residence time of the first mixing event is understood preferably the length of the time interval in which the polymer particles on average during the first mixing event are mixed with a liquid with a speed such that the kinetic energy of the polymer particles is on average larger than the adhesion energy between the individual polymer particles. A particularly economical operation of the mixer used for the first mixing event is achieved through the short mean residence time of the polymer particles in the first mixing event. In addition the formation of fines through mechanical abrasion is prevented by this short duration.

In a particular embodiment of the process according to the invention the static pressure build-up during the first mixing event amounts to less than about 0.1 bar, in particular less than about 0.05 bar, preferably less than about 0.01 bar. By means of these low static pressures a clumping of the polymer particles is prevented. By preventing a clumping a large surface area is provided which allows a rapid liquid absorption.

In order to increase the absorption rate, preferably water or an aqueous solution is added as the liquid. In a special embodiment of the invention the liquid comprises additives, in particular alcohols. In another special embodiment the liquid comprises no additives. In this special embodiment of the process according to the invention the liquid is in particular free from additives such as singly or multiply charged metal cations or water soluble organic substances with a viscosity within a range between about 200 and about 300 centistokes, wherein the liquid is in particular free from those substances which are concretely specified as additives in WO-A-98/49221. Free from additives in the sense of the above inventions means that the liquid comprises, besides the liquid as main component, these additives in quantities of less than about 500 ppm, preferably less than about 100 ppm, particularly preferably less than about 10 ppm, above all even more preferably less than about 1 ppm and most preferably less than about 0.1 ppm.

The polymer particles used in the process according to the invention preferably have an average particle size according to ERT 420.1-99 within a range from 10 to 10000 μm, particularly preferably within a range from about 50 to about 5000 μm and above all preferably within a range from about 100 to about 1000 μm.

It is further preferred that the polymer particles used in the process according to the invention have:
(α1) about 0.1 to about 99.999 wt. %, preferably about 20 to about 98.99 wt. % and particularly preferably about 30 to about 98.95 wt. % of polymerized, ethylenically unsaturated, acidic group-containing monomers or salts thereof, or polymerized, ethylenically unsaturated monomers containing a protonated or a quaternary nitrogen, or mixtures thereof, wherein at least ethylenically unsaturated, acidic group-containing monomers, preferably acrylic acid comprising mixtures are particularly preferred,
(α2) 0 to about 70 wt. %, preferably about 1 to about 60 wt. % and particularly preferably about 1 to about 40 wt. % of polymerized, ethylenically unsaturated monomers which can be co-polymerized with (α1),
(α3) about 0.001 to about 10 wt. %, preferably about 0.01 to about 7 wt. % and particularly preferably about 0.05 to about 5 wt. % of one or more cross-linkers,
(α4) 0 to about 30 wt. %, preferably about 1 to about 20 wt. % and particularly preferably about 5 to about 10 wt. % of water soluble polymers, as well as
(α5) 0 to about 20 wt. %, preferably about 0.01 to about 7 wt. % and particularly preferably about 0.05 to about 5 wt. % of one or more additives, wherein the sum of the component weights (α1) to (α5) amounts to 100 wt. %.

The monoethylenically unsaturated, acidic group-containing monomers (α1) can be partially or fully, preferably partially neutralized. The monoethylenically unsaturated acidic groups are neutralized preferably to at least about 25 mol %, particularly preferred to at least about 50 mol % and even more preferred to about 50 to about 90 mol %. The neutralization of the monomers (α1) can occur before and also after the polymerization. Furthermore, the neutralization can be carried out with alkali metal hydroxides, alkaline earth metal hydroxides, ammonia, as well as carbonates and bicarbonates. In addition any further base which forms a water soluble salt with the acid is conceivable. A mixed neutralization with different bases is also conceivable. Neutralization with ammonia or with alkali metal hydroxides is preferred, with sodium hydroxide or with ammonia is particularly preferred.

Furthermore the free acidic groups can predominate in a polymer, so that this polymer has a pH value lying in the acidic region. This acidic water-absorbing polymer can be at least partially neutralized by a polymer with free basic groups, preferably amino groups, which polymer is basic in comparison to the acidic polymer. These polymers are described in the literature as "Mixed-Bed Ion-Exchange Absorbent Polymers" (MBIEA-polymers) and are disclosed in WO 99/34843 among others. As a rule MBIEA-polymers produce a compound which comprises on the one hand basic polymers, which are in a position to exchange anions and on the other hand a polymer which is acidic in comparison to the basic polymer, said acidic polymer being in a position to exchange cations. The basic polymer has basic groups and is typically obtained by polymerization of monomers which carry basic groups or groups which can be converted into basic groups. With these monomers those which have primary, secondary or tertiary amines or the corresponding phosphines or at least two of the above functional groups are concerned above all. To this group of monomers belong particularly ethylenamine, allylamine, diallylamine, 4-aminobutene, alkyloxycycline, vinylformamide, 5-aminopentene, carbodiimide, formaldacine, melamine and the like, as well as secondary or tertiary amine derivatives thereof.

Preferred monoethylenically unsaturated, acidic group-containing monomers (α1) are acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbinic acid, α-chlorosorbinic acid, 2'-methylisocrotonic acid, cinnamic acid, p-chlorocinnamic acid, β-stearic acid, itaconic acid, citraconic acid, mesaconic acid, glutaconic acid, aconitic acid, maleic acid, fumaric acid, tricarboxythylene and maleic acid anhydride, where acrylic acid and methacrylic acid and above all acrylic acid are particularly preferred.

Besides these carboxylate group-containing monomers, further preferred monoethylenically unsaturated acidic group-containing monomers (α1) are ethylenically unsaturated sulfonic acid monomers or ethylenically unsaturated phosphonic acid monomers.

Preferred ethylenically unsaturated sulfonic acid monomers are allylsulfonic acid or aliphatic or aromatic vinylsulfonic acids or acrylic or methacrylic sulfonic acids. Preferred aliphatic or aromatic vinylsulfonic acids are vinylsulfonic acid, 4-vinylbenzylsulfonic acid, vinyltoluenesulfonic acid and styrenesulfonic acid. Preferred acrylic or methylacrylic sulfonic acids are sulfoethyl(meth)acrylate, sulfopropyl (meth)acrylate and 2-hydroxy-3-methacryloxypropylsulfonic acid. As (meth)acrylamidoalkylsulfonic acid, 2-acrylamido-2-methylpropansulfonic acid is preferred.

Additionally preferred are ethylenically unsaturated phosphonic acid monomers, such as vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acrylphosphonic acid derivatives.

Preferred ethylenically unsaturated monomers ($\alpha$1) containing a protonated nitrogen are dialkylaminoethyl(meth)acrylate-hydrochlorides in the protonated form, for example dimethylaminoethyl(meth)acrylate-hydrochloride or dimethylaminoethyl(meth)acrylate-hydrosulfate, as well as dialkylaminoalkyl(meth)acrylamides in the protonated form, for example dimethylaminoethyl(meth)acrylamide-hydrochloride, dimethylaminopropyl(meth)acrylamide-hydrochloride, dimethylaminopropyl(meth)acrylamide-hydrosulfate or dimethylaminoethyl(meth)acrylamide-hydrosulfate.

Preferred ethylenically unsaturated monomers ($\alpha$1) containing a quaternated nitrogen are dialkylammoniumalkyl(meth)acrylates in quaternated form, for example trimethylammoniumethyl(meth)acrylate-methosulfate or dimethylethylammoniumethyl(meth)acrylate-ethosulfate as well as (meth)acrylamidoalkyldialkylamines in quaternated form, for example (meth)acrylamidopropyltrimethylammonium chloride, trimethylammoniumethyl(meth)acrylate chloride and (meth)acrylamidopropyltrimethylammonium sulfate.

According to the invention it is preferred that the polymer comprise at least about 50 wt. %, preferably at least about 70 wt. % and above all preferably at least 90 wt. % carboxylate group-containing monomers. According to the invention it is particularly preferred that the polymer comprise at least about 50 wt. %, preferably at least about 70 wt. % acrylic acid, which is neutralized preferably to at least about 20 mol % and particularly preferably to at least about 50 mol %.

Preferred monoethylenically unsaturated monomers ($\alpha$2) which can be co-polymerized with ($\alpha$1) are acrylamides and (meth)acrylamides.

Possible (meth)acrylamides besides acrylamide and methacrylamide are alkyl-substituted (meth)acrylamides or aminoalkylsubstituted derivatives of (meth)acrylamides such as N-methylol(meth)acrylamide, N,N-dimethylamino(meth)acrylamide, dimethyl(meth)acrylamide or diethyl(meth)acrylamide. Possible vinylamides are for example N-vinylamides, N-vinylformamides, N-vinylacetamides, N-vinyl-N-methylacetamide, N-vinyl-N-methylformamides, vinylpyrrolidone. Among these monomers acrylamide is particularly preferred.

Further preferred monoethylenically unsaturated monomers ($\alpha$2) which are copolymerizable with ($\alpha$1) are water dispersible monomers. Preferred water dispersible monomers are acrylic acid esters and methacrylic acid esters, such as methyl(meth)acrylate, ethyl(meth)acrylate, propyl(meth)acrylate or butyl(meth)acrylate, as well as vinylacetate, styrene and isobutylene.

Preferred cross-linkers ($\alpha$3) according to the invention are compounds which have at least two ethylenically unsaturated groups in one molecule (cross-linker class I), compounds which have at least two functional groups which can react with functional groups of the monomers ($\alpha$1) or ($\alpha$2) in a condensation reaction (=condensation cross-linkers), an addition reaction or a ring-opening reaction (cross-linker class II), compounds which have at least one ethylenically unsaturated group and at least one functional group which can react with functional groups of the monomers ($\alpha$1) or ($\alpha$2) in a condensation reaction, an addition reaction or a ring-opening reaction (cross-linker class III), or polyvalent metal cations (cross-linker class (IV). Thereby a cross-linking of the polymer is achieved with the compounds of cross-linker class I by radical polymerization of the ethylenically unsaturated groups of the cross-linker molecules with the monoethylenically unsaturated monomers ($\alpha$1) or ($\alpha$2), while with the compounds of cross-linker class II and the polyvalent metal cations of cross-linker class IV a cross-linking of the polymer is achieved via condensation reaction of the functional groups (cross-linker class II) or via electrostatic interaction of the polyvalent metal cation (cross-linker class IV) with the functional groups of the monomer ($\alpha$1) or ($\alpha$2). With compounds of cross-linker class III a cross-linking of the polymers is achieved correspondingly by radical polymerization of the ethylenically unsaturated groups or just as well by condensation reaction between the functional groups of the cross-linkers and the functional groups of the monomers ($\alpha$1) or ($\alpha$2).

Preferred compounds of cross-linker class I are poly(meth)acrylic acid esters, which have been obtained for example by conversion of a polyol, such as for example ethylene glycol, propylene glycol, trimethylolpropane, 1,6-hexanediol, glycerin, pentaerythritol, polyethyleneglycol or polypropyleneglycol, of an aminoalcohol, a polyalkylenepolyamine, such as for example diethylenetriamine or triethylenetetraamine, or of an alkoxidized polyol with acrylic acid or methacrylic acid. Further preferred compounds of cross-linker class I are polyvinyl compounds, poly(meth)allyl compounds, (meth)acrylic acid esters of a monovinyl compound or (meth)acrylic acid esters of a mono(meth)allyl compound, preferably of the mono(meth)allyl compounds of a polyol or of an aminoalcohol. In this context reference is made to DE 195 43 366 and DE 195 43 368.

As examples of compounds of cross-linker class I are named alkenyldi(meth)acrylates, for example ethyleneglycoldi(meth)acrylate, 1,3-propyleneglycoldi(meth)acrylate, 1,4-butyleneglycoldi(meth)acrylate, 1,3-butyleneglycoldi(meth)acrylate, 1,6-hexanedioldi(meth)acrylate, 1,10-decanedioldi(meth)acrylate, 1,12-dodecanedioldi(meth)acrylate, 1,18-octadecanedioldi(meth)acrylate, cyclopentanedioldi(meth)acrylate, neopentylglycoldi(meth)acrylate, methylenedi(meth)acrylate or pentaerythritoldi(meth)acrylate, alkenyldi(meth)acrylamides, for example N-methyldi(meth)acrylamide, N,N'-3-methylbutylidenebis(meth)acrylamide, N,N'-(1,2-dihydroxyethylene)bis(meth)acrylamide, N,N'-hexamethylenebis(meth)acrylamide or N,N'-methylenebis(meth)acrylamide, polyalkoxydi(meth)acrylates, for example diethyleneglycoldi(meth)acrylate, triethyleneglycoldi(meth)acrylate, tetraethyleneglycoldi(meth)acrylate, dipropyleneglycoldi(meth)acrylate, tripropyleneglycoldi(meth)acrylate or tetrapropyleneglycoldi(meth)acrylate, bisphenol-A-di(meth)acrylate, ethoxylated bisphenol-A-di(meth)acrylate, benzylidenedi(meth)acrylate, 1,3-di(meth)acryloyloxypropanol-2, hydroquinonedi(meth)acrylate, di(meth)acrylate esters of trimethylolpropane, which are preferably alkoxylated with 1 to 30 mol alkylene oxide per hydroxyl group, preferably ethoxylated, thioethyleneglycoldi(meth)acrylate, thiopropyleneglycoldi(meth)acrylate, thiopolyethyleneglycoldi(meth)acrylate, thiopolypropyleneglycoldi(meth)acrylate, divinyl ethers, for example 1,4-butanedioldivinylether, divinyl esters, for example divinyladipate, alkanedienes, for example butadiene or 1,6-hexadiene, divinylbenzene, di(meth)allyl compounds, for example di(meth)allylphthalate or di(meth)

allylsuccinate, homo- and co-polymers of di(meth)allyldimethylammonium chloride and homo- and co-polymers of diethyl(meth)allylaminomethyl(meth)acrylateammonium chloride, vinyl(meth)acrylic compounds, for example vinyl (meth)acrylate, (meth)allyl(meth)acrylic compounds, for example (meth)allyl(meth)acrylate, (meth)allyl(meth)acrylate ethoxylated with 1 to 30 mol ethylene oxide per hydroxyl group, di(meth)allylesters of polycarbonic acids, for example di(meth)allylmaleate, di(meth)allylfumarate, di(meth)allylsuccinate or di(meth)allylterephthalate, compounds with 3 or more ethylenically unsaturated, radically polymerizable groups such as for example glycerine tri(meth)acrylate, (meth)acrylate esters of glycerins ethoxylated with preferably 1 to 30 mol ethylene oxide per hydroxyl group, trimethylolpropanetri(meth)acrylate, tri(meth)acrylate esters of trimethylolpropane which is alkoxylated preferably with 1 to 30 mol alkylene oxide per hydroxide group, preferably ethoxylated, trimethacrylamide, (meth)allylidenedi(meth)acrylate, 3-allyloxy-1,2-propanedioldi(meth)acrylate, tri(meth)allylcyanurate, tri(meth)allylisocyanurate, pentaerythritoltetra (meth)acrylate, pentaerythritoltri(meth)acrylate, (meth) acrylic acid esters of pentaerythritol which is ethoxylated with preferably 1 to 30 mol ethylene oxide per hydroxyl group, tris(2-hydroxyethyl)isocyanuratetri(meth)acrylate, trivinyltrimellitate, tri(meth)allylamine, di(meth)allylalkylamines, for example di(meth)allylmethylamine, tri(meth)allylphosphate, tetra(meth)allylethylenediamine, poly(meth)allyl ester, tetra(meth)allyloxyethane or tetra(meth)allylammonium halides.

Preferred compounds of cross-linker class II are compounds which have at least two functional groups which can react with the functional groups of the monomers (α1) or (α2), preferably with acidic groups of the monomers (α1), in a condensation reaction (=condensation cross-linkers), in an addition reaction or in a ring opening reaction. Examples of these functional groups of the compounds of cross-linker class II are preferably alcoholic, amino, aldehyde, glycidic, isocyanate, carbonate or epichloro functions.

As examples of compounds of cross-linker class II are mentioned polyols, for example ethyleneglycol, polyethyleneglycols such as diethyleneglycol, triethyleneglycol and tetraethyleneglycol, propyleneglycol, polypropyleneglycols such as dipropyleneglycol, tripropyleneglycol or tetrapropyleneglycol, 1,3-butanediol, 1,4-butanediol, 1,5-pentanediol, 2,4-pentanediol, 1,6-hexanediol, 2,5-hexanediol, glycerine, polyglycerin, trimethylolpropane, polyoxypropylene, oxyethylene-oxypropylene-block copolymer, sorbitan-fatty acid esters, polyoxyethylenesorbitan-fatty acid esters, pentaerythritol, polyvinylalcohol and sorbitol, aminoalcohols, for example ethanolamine, diethanolamine, triethanolamine or propanolamine, polyamine compounds, for example ethylenediamine, diethylenetriamine, triethylenetetraamine, tetraethylenepentaamine or pentaethylenehexaamine, polyglycidyl ether compounds such as ethyleneglycoldiglycidyl ether, polyethyleneglycoldiglycidyl ether, glycerinediglycidyl ether, glycerinepolyglycidyl ether, pentaerithritolpolyglycidyl ether, propyleneglycoldiglycidyl ether, polypropyleneglycoldiglycidyl ether, neopentylglycoldiglycidyl ether, hexanediolglycidyl ether, trimethylolpropanepolyglycidyl ether, sorbitolpolyglycidyl ether, phthalic acid diglycidyl ester, adipinic acid diglycidyl ether, 1,4-phenylenebis(2-oxazoline), glycidol, polyisocyanates, preferably diisocyanates such as 2,4-toluenediioscyanate and hexamethylenediisocyanate, polyaziridine compounds such as 2,2-bishydroxymethylbutanol-tris[3-(1-aziridinyl)propionate], 1,6-hexamethylenediethyleneurea and diphenylmethane-bis-4,4'-N,N'-diethyleneurea, halogen epoxides for example epichloro- and epibromohydrin and α-methylepichlorohydrin, alkylenecarbonates such as 1,3-dioxolane-2-one (ethylene carbonate), 4-methyl-1,3-dioxolane-2-one (propylene carbonate), 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxolane-2-one, poly-1,3-dioxolane-2-one, polyquaternary amines such as condensation products from dimethylamines and epichlorohydrin. Further preferred compounds of the cross-linker class II are in addition polyoxazolines such as 1,2-ethylenebisoxazoline, cross-linkers with silane groups such as γ-glycidooxypropyltrimethoxysilane and γ-aminopropyltrimethoxysilane, oxazolidinones such as 2-oxazolidinone, bis- and poly-2-oxazolidinone and diglycolsilicates.

Preferred compounds of class III are hydroxyl or amino group-containing esters of (meth)acrylic acid, such as for example 2-hydroxyethyl(meth)acrylate, as well as hydroxyl or amino group-containing (meth)acrylamides, or mono (meth)allylic compounds of diols.

The polyvalent metal cations of the cross-linker class IV are derived preferably from singly or multiply charged cations. Particularly preferred doubly charged cations are derived from zinc, beryllium, alkaline earth metals such as magnesium, calcium, strontium, wherein magnesium is preferred. Further applicable cations with higher charge are cations from aluminium, iron, chromium, manganese, titanium, zirconium and other transition metals as well as double salts of such cations or mixtures of the named salts. The use of aluminium salts and alums and various hydrates thereof such as e.g. $AlCl_3 \times 6\ H_2O$, $NaAl(SO_4)_2 \times 12H_2O$, $KAl(SO_4)_2 \times 12H_2O$ or $Al_2(SO_4)_3 \times 14\text{-}18H_2O$ is preferred.

The use of $Al_2(SO_4)_3$ and its hydrates as cross-linkers of the cross-linker class IV is particularly preferred.

Preferred polymer particles are polymer particles, which are cross-linked by cross-linkers of the following cross-linker classes or by cross-linkers of the following combinations of cross-linker classes: I, II, III, IV, I II, I III, I IV, I II III, I II IV, I III IV, II III IV, II IV or III IV. The above combinations of cross-linker classes produce respectively a preferred embodiment of cross-linkers of a polymer particle.

Further preferred embodiments of the polymer particles are polymer particles, which are cross-linked by any of the above named cross-linkers of cross-linker class I. Among these, water soluble cross-linkers are preferred. In this context, N,N'-methylenebisacrylamide, polyethyleneglycoldi(meth)acrylate, triallylmethylammonium chloride, tetraallylammonium chloride as well as allyinonaethyleneglycolacrylate made with 9 mol ethylene oxide per mol acrylic acid are particularly preferred.

The water-absorbent polymers can be produced from the above-named monomers and cross-linkers by various polymerization means. For example, in this context can be named bulk polymerization which occurs preferably in kneading reactors such as extruders, belt polymerization, solution polymerization, spray polymerization, inverse emulsion polymerization and inverse suspension polymerization. Solution polymerization is preferably carried out in water as solvent. The solution polymerization can occur continuously or discontinuously. From the prior art a broad spectrum of variation possibilities can be gathered with respect to reaction proportions such as temperature, type and quantity of the initiators as well as of the reaction solution. Typical processes are described in the following patent specifications: U.S. Pat. No.

4,286,082, DE 27 06 135, U.S. Pat. No. 4,076,663, DE 35 03 458, DE 40 20 780, DE 42 44 548, DE 43 23 001, DE 43 33 056, DE 44 18 818.

The polymerization is initiated by an initiator as is generally customary. All initiators forming radicals under the polymerization conditions can be used as initiators for the initiation of the polymerization, which initiators are customarily used in production superabsorbers. An initiation of the polymerization by action of electron beams on the polymerizable aqueous solution is also possible. The polymerization can be initiated in the absence of initiators of the above-mentioned type by action of energetic beams in the presence of photo-initiators. Polymerization initiators can be used dissolved or dispersed in a solution of monomer according to the invention. All compounds known to one experienced in the art to decompose into radicals can be used as initiators. Hereunder fall in particular peroxides, hydroperoxides, hydrogen peroxide, persulfates, azo compounds as well as the so-called redox catalysts. Preferred is the use of water soluble catalysts. In some cases it is advantageous to use mixtures of different polymerization initiators. Among these mixtures those initiators comprising hydrogen peroxide and sodium or potassium peroxodisulfate, which can be used in any conceivable quantity ratio, are preferred. Suitable organic peroxides are preferably acetylacetone peroxide, methylethylketone peroxide, t-butylhydroperoxide, cumolhydroperoxide, t-amylperpivalate, t-butylperpivalate, t-butylpemeohexonate, t-butylisobutyrate, t-butylper-2-ethylhexenoate, t-butylperisononanoate, t-butylpermaleate, t-butylperbenzoate, t-butyl-3,5,5-trimethylhexanoate and amylpemeodecanoate. Additionally preferred as polymerization initiators are: azo compounds, such as 2,2'-azobis(2-amidinopropane)-dihydrochloride, azo-bisamidinopropane-dihydrochloride, 2,2'-azobis(N,N-dimethylene)isobutyramidine-dihydrochloride, 2-(carbamoylazo)isobutyronitrile and 4,4'-azobis(4-cyanovaleric acid). The compounds mentioned are used in normal quantities, preferably within a range from about 0.001 to about 5, preferably from about 0.1 to about 2 mol %, respectively based on the quantity of the monomers to be polymerized.

The redox catalysts have as oxidic components at least one of the above-indicated per-compounds and as reducing components preferably ascorbic acid, glucose, sorbose, mannose, ammonium or alkali metal hydrogensulfite, -sulfate, -thiosulfate, -hyposulfite or -sulfide, metal salts, such as iron(II) ions or silver ions or sodium hydroxymethylsulfoxylate. Preferably used as reducing components of the redox catalysts are ascorbic acid or sodium pyrosulfite. Based on the quantity of monomers to be used in the polymerization, about $1 \times 10^{-5}$ to about 1 mol % of the reducing component of the redox catalyst and about $1 \times 10^{-5}$ to about 5 mol % of the oxidizing component of the redox catalyst are used. In place of the oxidizing components of the redox catalyst, or in addition thereto, one or more preferably water soluble azo compounds can be used.

If the polymerization is initiated by action of energetic beams, so-called photo-initiators are generally used. These can comprise for example so-called α-splitters, H-abstracting systems or also azides. Examples of such initiators are benzophenone derivatives such as Michler's ketone, phenanthrene derivatives, fluorine derivatives, anthraquinone derivatives, thioxanthone derivatives, cumarin derivatives, benzoinether and derivatives thereof, azo compounds such as the above-mentioned radical formers, substituted hexaarylbisimidazoles or acylphosphine oxides. Examples of azides are: 2-(N,N-dimethylamino)ethyl-4-azidocinnamate, 2-(N,N-dimethylamino)ethyl-4-azidonaphthylketone, 2-(N,N-dimethylamino)ethyl-4-azidobenzoate, 5-azido-1-naphthyl-2'-(N,N-dimethylamino)ethylsulfone, N-(4-sulfonylazidophenyl)maleinimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. The photo-initiators, when used, are generally employed in quantities from about 0.01 to about 5 wt. % based on the monomers to be polymerized.

A redox system used preferentially according to the invention comprises hydrogen peroxide, sodium peroxodisulfate and ascorbic acid. Generally azo compounds are preferred as initiators according to the invention, wherein azo-bis(amidinopropane) dihydrochloride is particularly preferred. As a rule the polymerization is initiated with the initiators in a temperature range of about 30 to about 90° C.

After producing the water-absorbent polymers these polymers are dried and broken up to form the above-described polymer particles.

As water soluble polymers (α4), water soluble polymerizates such as those comprising partly or fully saponified polyvinyl alcohol, polyvinylpyrrolidone, starches or starch derivatives, polyglycols or polyacrylic acids can preferably be polymerized into the polymer particles. The molecular weight of these polymers is not critical, as long as they are water soluble. Preferred water soluble polymers are starches or starch derivatives or polyvinyl alcohol. The water soluble polymers, preferably synthetic polymers like polyvinyl alcohol, can also serve as graft basis for the monomers to be polymerized.

Additives (α5) to the polymer particles used in the process according to the invention can comprise preferably suspension agents, odour binders, surface-active agents, or antioxidants. These additives (α5) are preferably added before the polymerization of the monomer solution or mixed with the polymer particles after producing said particles, wherein for the mixing, mixing aggregates known to one skilled in the art can be used, for example the Patterson-Kelley mixer, DRAIS turbulence mixer, Lödige mixer, Ruberg mixer, screw mixer, pan mixer and fluidized bed mixer as well as continually functioning vertical mixers, in which the polymer particles and the additives (α5) are mixed with a fast frequency by means of rotating knives (Schugi mixer).

In another embodiment of the process according to the invention the outer portion of the absorbent polymer particles is brought into contact with a compound comprising $Al^{3+}$ ions.

Therein it is preferred that the compound comprising $Al^{3+}$ ions in a quantity within a range from about 0.01 to about 30 wt. %, particularly preferred in a quantity within a range from about 0.1 to about 20 wt. % and above all preferred in a quantity within a range from about 0.3 to about 5 wt. %, respectively based on the weight of the absorbent polymer particles, is brought into contact with the polymer particles.

Preferably the absorbent polymer particles are brought into contact with the $Al^{3+}$ ion-containing compound, by bringing this compound, in the form of a fluid comprising the $Al^{3+}$ ion-containing compound as well as a solvent such as methanol or ethanol or mixtures of at least two therefrom, into contact with the polymer particles. The $Al^{3+}$ ion-containing compound is thereby present in the fluid, without consideration of water of crystallization, preferably in a quantity within a range from about 0.1 to about 50 wt. %, preferably in a quantity within a range from about 1 to about 30 wt. %, respectively based on the total weight of the fluid. It is further preferred that the fluid, in a quantity within a range from about 0.01 to about 15 wt. %, preferably in a quantity within a range from about 0.05 to about 6 wt. % respectively based on the weight of the absorbent polymer particles, is brought into contact with the absorbent polymer particles.

Preferred compounds comprising $Al^{3+}$ ions are $AlCl_3 \times 6H_2O$, $NaAl(SO_4)_2 \times 12H_2O$, $KAl(SO_4)_2 \times 12H_2O$ or $Al_2(SO_4)_3 \times 14\text{-}18H_2O$.

In a further embodiment of the process according to the invention the liquid, with which in the first mixing event the polymer particles are mixed and which in the second mixing event is homogenized within the polymer particles, comprises an $Al^{3+}$ ion-containing compound. Preferred $Al^{3+}$ ion-containing compounds are $AlCl_3 \times 6H_2O$, $NaAl(SO_4)_2 \times 12H_2O$, $KAl(SO_4)_2 \times 12H_2O$ or $Al_2(SO_4)_3 \times 14\text{-}18H_2O$.

It is furthermore preferred according to the invention that the polymer particles used in the process according to the invention have an inner portion, an outer portion surrounding the inner portion as well as a surface portion surrounding the outer portion, wherein the outer portion has a higher degree of cross-linking than the inner portion, so that preferably a nucleus-shell structure forms. The increased cross-linking in the surface portion of the polymer particle used is therein preferably accomplished by secondary cross-linking of reactive groups close to the surface. This secondary cross-linking can occur thermally, photochemically or chemically. As secondary cross-linkers for the chemical secondary cross-linking are therein preferred the compounds (α3) which were mentioned as cross-linkers of the cross-linker classes II and IV. Ethylene carbonate is particularly preferred as secondary cross-linker.

The secondary cross-linkers are preferably used in the cross-linking in a quantity within a range from about 0.01 to about 30 wt. %, particularly preferably in a quantity within a range from about 0.1 to about 20 wt. % and above all preferably in a quantity within a range from about 0.3 to about 5 wt. % respectively based on the weight of the polymer particles used in the process according to the invention.

The secondary cross-linking preferably occurs thus, that a fluid $F_1$ comprising a solvent, preferably water, water-miscible organic solvents such as methanol or ethanol or mixtures of at least two thereof, as well as the secondary cross-linker, is brought into contact with the outer portion of the polymer particles at a temperature within a range from about 30 to about 300° C., particularly preferred within a range from about 100 to about 200° C. The bringing into contact therein occurs preferably by spraying the fluid onto the polymer particles and then mixing the polymer particles which have been brought into contact with the fluid $F_1$. Therein the secondary cross-linker in the fluid $F_1$ is present preferably in a quantity within a range from about 0.01 to about 20 wt. %, particularly preferably in a quantity within a range from about 0.1 to about 10 wt. %, based on the total weight of the fluid $F_1$. It is further preferred that the fluid $F_1$ be brought into contact with the polymer particles in a quantity within a range from about 0.01 to about 50 wt. %, particularly preferred in a quantity within a range from about 0.1 to about 30 wt. %, respectively based on the weight of polymer particles.

If the absorbent polymer particles are brought into contact with an $Al^{3+}$ ion-containing compound, it is further preferred that the polymer particles in the case of a secondary cross-linking are brought into contact with the $Al^{3+}$ ion-containing compound before carrying out the secondary cross-linking. Therein the absorbent polymer particles can first be brought into contact with a fluid comprising the $Al^{3+}$ ion-containing compound and then with a fluid comprising the cross-linker. It is also conceivable to bring the $Al^{3+}$ ion-containing compound and the cross-linker in a common fluid into contact with the absorbent polymer particles and then to effect the secondary cross-linking by increasing the temperature. The decisive factor is merely that the bringing into contact of the absorbent polymer particles with the $Al^{3+}$ ion-containing compound occurs before carrying out the secondary cross-linking reaction.

It is furthermore preferred that the polymer particles used in the process according to the invention have at least one of the following properties:

(A) the maximum absorption of 0.9 wt. % NaCl solution according to ERT 440.1-99 is within a range from at least about 10 to about 1000, preferably from about 15 to about 500 and particularly preferred from about 20 to about 300 g/g, (B) the part extractable with 0.9 wt. % NaCl solution according to ERT 470.1-99 amounts to less than about 30, preferably less than about 20 and particularly preferred less than about 10 wt. %, based on the polymer particles, (C) The bulk density according to ERT 460.1-99 is within a range from about 300 to about 1000, preferably about 310 to about 800 and particularly preferred about 320 to about 700 g/l, (D) The pH value according to ERT 400.1-99 for 1 g of the polymer particles in 1 l water is within a range from about 4 to about 10, preferably about 5 to about 9 and particularly preferably about 5.5 to about 7.5.

(E) The CRC value according to ERT 441.1-99 is within a range from about 10 to about 100, preferably about 15 to about 80 and particularly preferably about 20 to about 60 g/g.

(F) The AAP value according to ERT 442.1-99 under a pressure of 0.7 psi (50 g/cm$^2$) is within a range from about 10 to about 60, preferably about 15 to about 50 and particularly preferably about 20 to about 40 g/g.

(G) The AAP value according to ERT 442.1-99 under a pressure of 0.3 psi (20 g/cm$^2$) is within a range from about 10 to about 100, preferably about 15 to about 60 and particularly preferably about 20 to about 50 g/g.

The property combinations of two or more properties arising from the above properties represent respectively preferred embodiments of the process according to the invention.

Further particularly preferred embodiments are processes, in which the polymer particles used in the process according to the invention have the following properties or combinations of properties depicted as alphabetic characters or combinations of alphabetic characters: A, B, C, D, E, F, G, AB, AC, AD, AE, AF, AG, EF, EG, FG, ABC, ABD, ABE, ABF, ABG, ACD, ACE, ACF, ACG, ADE, ADF, ADG, AEF, AEG, CEF, CEG, EFG, ABCD, ABCE, ABCF, ABCG, ABDE, ABDF, ABDG, ACDE, ACDF, ACDG, ACEF, ACEG, ADEF, ADEG, CEFG, ACDEF, ACDEG, ABDEF, ABDEG, ABCEF, ABCEG, ACBDF, ACBDG, ABCDE, ABCDEF, ABCDEG or ABCDEFG, wherein the combination CEFG is particularly preferred and the combination EF is even more preferred.

Referring now to the Figures, which illustrate preferred embodiments and particularities which can occur individually or in combination, it should be understood that the illustrations do not limit the invention and should only exemplify the invention.

FIG. 1 shows that in the first mixing event a polymer particle (1) is mixed with liquid (2). The surface of the polymer particle (1) is thus wetted with liquid (2) and a liquid (2)—wetted polymer particle (3) formed. In the second mixing event the liquid (2) penetrates the wetted polymer particle (3) into the inside of the polymer particle (1). Thereby the liquid (2) is homogeneously distributed within the polymer particles. The polymer particle (1) swells somewhat. The homogenization of the liquid (2) within the polymer particle (1) causes a faster absorption of water.

Figure 2:
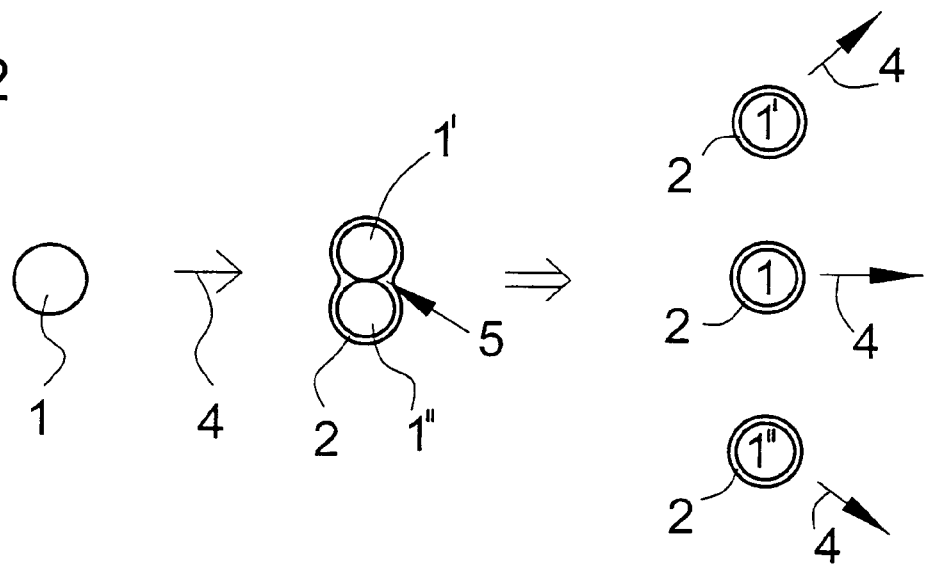
FIG. 2 illustrates a collision between a polymer particle and two stuck-together polymer particles during the first mixing event.

FIG. 2 shows as an example a collision between a polymer particle (1) and two stuck-together polymer particles (1', 1"). Both of the stuck-together polymer particles (1', 1") are held together by various factors such as for example cohesion or adhesion of the liquid (2) and the polymer particles (1', 1"). An adhesion layer (5) between the surfaces of both polymer particles (1', 1") causes a further binding effect between both polymer particles (1', 1"). By means of the high speed of the approaching polymer particle (1) the adhesion between both stuck-together polymer particles (1') and (1") is overcome. In particular the adhesion layer is broken open. The result of the collision is a separation of the one stuck-together polymer particle (1') from the other stuck-together polymer particle (1"), so that after the collision (4) the polymer particles (1, 1', 1") continue to move individually. An even wetting of the surfaces is achieved by means of the collision.

The process according to the invention for producing an absorbent polymer has a first mixing event, in which a plurality of absorbent polymer particles (1) is mixed with a liquid (2) and a second mixing event, in which the liquid (2) is homogenized within the polymer particles (1), wherein the polymer particles (1) are mixed in the first mixing event with a speed such that the kinetic energy of the individual polymer particles (1) is on average larger than the adhesion energy between the individual polymer particles (1), and the polymer particles (1) in the second mixing event are stirred at a lower speed than in the first mixing event. The different speeds effect a fluidization of the polymer particles (1), which fluidization prevents a clumping of the polymer particles (1) during the mixing event. The absorbent polymer thus prepared or a composite or a chemical product, comprising a polymer of this type, distinguishes itself by a particularly rapid swelling behavior.

The invention comprises furthermore the absorbent polymers obtainable by the process according to the invention.

The invention comprises also an absorbent polymer, which is preferably obtainable by the process according to the invention, comprising water in a quantity within a range from about 0.1 to about 20 wt. %, preferably within a range from about 0.5 to about 15 wt. % and above all preferably in a range from about 1 to about 5 wt. %, respectively determined according to the oven method according to ERT 430.1-99 and respectively based on the total weight of the absorbent polymer, which has at least one of the following properties:

(A1) an AAP value according to ERT 442.1-99 under a pressure of 0.7 psi (50 g/cm$^2$) within a range from about 10 to about 60, preferably about 15 to about 50 and particularly preferably about 20 to about 40 g/g, (B1) an AAP value according to ERT 442.1-99 under a pressure of 0.3 psi (20 g/cm$^2$) within a range from about 10 to about 100, preferably about 15 to about 60 and particularly preferred about 20 to about 50 g/g, (C1) a CRC value according to ERT 441.1-99 within a range from about 10 to about 100 g/g, preferably within a range from about 15 to about 50 g/g and particularly preferred within a range from about 17 to about 40 g/g, (D1) a drop determined according to the herein-described method of the AAP value determined according to ERT 442.1-99 under a pressure of 0.7 psi after a degradation through mechanical stress of less than about 20%, particularly preferred of less than about 15 wt. % and above all preferred of less than about 10%, (E1) in a composite of 50 wt. % of the absorbent polymer, 47.5 wt. % of cellulose fibers and 2.5 wt. % of a two-component fibre of polypropylene and polyethylene an absorption time after a first wetting, determined according to the herein described test method, of less than about 53 seconds, preferably less than about 50 seconds and particularly preferred less than about 46 seconds, (F1) in a composite of 50 wt. % of the absorbent polymer, 47.5 wt. % of cellulose fibers and 2.5 wt. % of a two-component fiber of polypropylene and polyethylene an absorption time after a second wetting, determined according to the herein described test method, of less than about 253 seconds, preferably less than about 225 seconds and particularly preferred less than about 200 seconds, (G1) in a composite of 50 wt. % of the absorbent polymer, 47.5 wt. % of cellulose fibers and 2.5 wt. % of a two-component fiber of polypropylene and polyethylene an absorption time after a third wetting, determined according to the herein described test method, of less than about 475 seconds, preferably less than about 450 seconds and particularly preferred less than about 400 seconds, (H1) in a composite of 50 wt. % of the absorbent polymer, 47.5 wt. % of cellulose fibers and 2.5 wt. % of a two-component fiber of polypropylene and polyethylene a rewet value, determined according to the herein described test method, of less than about 12.55 g/g, preferably less than about 12 g/g and particularly preferably less than about 11 g/g, wherein the water is homogeneously distributed in the absorbent polymer.

Preferred absorbent polymers are those polymers which are characterized by the following properties or property combinations: A1, B1, C1, D1, E1, F1, G1, H1, A1B1, A1C1, A1D1, B1C1, B1D1, C1D1, A1B1C1, A1B1D1, A1C1D1, B1C1D1, A1B1C1D1, E1F1, E1F1G1, F1G1, E1F1G1H1, F1G1H1, G1H1, D1E1F1G1H1, D1E1F1G1, D1E1F1, D1E1, D1H1, wherein D1 is particularly preferred.

It is furthermore preferred, that the absorbent polymers according to the invention have the same properties as the polymers obtainable by the process according to the invention. It is furthermore preferred, that according to an embodiment according to the invention of the process according to the invention as well as the absorbent polymer according to the invention the values of characteristics according to the invention given only with a lower limit have an upper limit, which is about 20 times, preferably about 10 times and particularly preferably about 5 times the most preferred value of the lower limit.

The invention also comprises a composite comprising the absorbent polymers according to the invention as well as a substrate. It is preferred that the absorbent polymers according to the invention and the substrate are securely bound together. As substrate are preferred films made out of polymers, such as for example out of polyethylene, polypropylene or polyamide, metals, fleece, fluff, tissues, fabric, natural or synthetic fibers, or other foams. Preferred composites according to the invention are sealant materials, cables, absorbent cores as well as diapers and hygiene articles comprising them.

Sealant materials are preferably water-absorbent films, wherein the absorbent polymer is worked into a polymer matrix or fiber matrix as substrate. This is carried out preferably by mixing the absorbent polymer with a polymer or fiber matrix-forming polymer (Pm) and finally binding them, optionally by thermal treatment. In the case where the absorbent structure is used as fibers, threads/yarns can be obtained therefrom which can be spun with additional fibers comprising another material as substrate and then for example bound together by knitting or weaving or be directly bound together, i.e. without being spun with additional fibers. Typical processes herefor are described in H. Savano et al., International Wire & Cable Symposium Proceedings 40, 333 to 338 (1991); M. Fukuma et al., International Wire & Cable Symposium Proceedings, 36, 350 to 355 (1987) and in U.S. Pat. No. 4,703,132.

In the embodiment in which the composite is a cable, the absorbent polymer as particles can be directly used, preferably beneath the insulation of the cable. In another embodiment of the cable the absorbent polymer (Pa) can be used in the form of swellable tension-resistant yarns. According to another embodiment of the cable the absorbent polymer can be used as swellable film. Furthermore in another embodiment of the cable the absorbent polymer can be used as moisture-absorbent cores in the middle of cables. The substrate in the case of the cable forms all components of the cable which contain no absorbent polymer. Hereunder are included conduits, such as electrical lines or light conduits, optical or electrical insulation materials as well as components of the cable which ensure the mechanical applicability of the cable, such as networks, fibers or fabrics made from tension-resistant materials such as synthetic materials and insulators made from rubber or other materials which prevent the destruction of the exterior of the cable.

If the composite is an absorbent core, the absorbent polymer is worked into a substrate. This substrate can preferably be in the form of fibrous materials. Fibrous materials which can be used in the present invention comprise natural fibers (modified or unmodified) as well as synthetic fibers. Examples of suitable unmodified and modified natural fibers comprise cotton, Esparto grass, sugarcane, kemp, flax, silk, wool, cellulose, chemically modified pulp, jute, rayon, ethylcellulose and cellulose acetate. Suitable synthetic fibers can be produced from polyvinylchloride, polyvinylfluoride, polytetrafluoroethylene, polyvinylidenechloride, polyacrylates such as Orion®, polyvinylacetate, polyethylvinylacetate, insoluble or soluble polyvinylalcohol, polyolefins such as polyethylene (for example PULPEX®) and polypropylenes, polyamides such as nylon, polyesters such as DACRON® or Kodel®, polyurethanes, polystyrenes and the like. The fibers used can comprise only natural fibers, only synthetic fibers or any compatible combination of natural and synthetic fibers.

The fibers used in the present invention can be hydrophilic or hydrophobic, or they can comprise a combination of hydrophilic and hydrophobic fibers. The term "hydrophilic" as used here describes fibers or surfaces of fibers which can be wetted by aqueous liquids (for example aqueous body liquids) which are deposited on these fibers. Hydrophilicity and wettability are typically defined in terms of the contact angle and the surface tension of the concerned liquids and solids. This is discussed in detail in a publication of the American Chemical Society with the title "Contact Angle, Wettability and Adhesion", published by Robert F. Gould (copyright 1964). A fiber or the surface of a fiber is wetted by a liquid (i.e. it is hydrophilic) if either the contact angle between the liquid and the fiber or the surface thereof amounts to less than about 90°, or if the liquid tends to distribute itself spontaneously over the surface, wherein both conditions are normally simultaneous. On the other hand a fiber or the surface of a fiber is considered as hydrophobic, if the contact angle is larger than about 90° and the liquid does not spread spontaneously on the surface of the fiber.

Preferred fibers according to the invention are hydrophilic fibers. Suitable hydrophilic fibers comprise cellulose fibers, modified cellulose fibers, rayon, polyester fibers, such as polyethyleneterephthalate (for example DACRON®), hydrophilic nylon (HYDROFIL®) and the like. Suitable hydrophilic fibers can also be obtained by hydrophilising hydrophobic fibers, such as surface-active agent-treated or silica-treated thermoplastic fibers, which are derived for example from polyolefins such as polyethylene or polypropylene or on polyacrylates, polyamides, polystrenes, polyurethanes and the like. For reasons of availability and of cost cellulose fibers, in particular pulp fibers, are preferred for use in the present invention. Further preferred hydrophilic fibers for use in the present invention are chemically stiffened cellulose fibers. The term "chemically stiffened cellulose fibers" describes therein cellulose fibers which are stiffened by means of a chemical medium in order to increase the stiffness of the fibers under dry as well as under aqueous conditions. Such media can comprise a chemical stiffening agent, which for example covers and/or impregnates the fibers. Such a medium can also comprise the stiffening of the fibers by changing the chemical structure, for example by cross-linking of polymer chains. Polymer-stiffening agents which can cover or impregnate the cellulose fibers comprise: cationic starches which have nitrogen-containing groups (for example amino groups), which are obtainable from the National Starch and Chemical Corp., Bridgewater, N.J., USA, latexes, moisture-resistant resins such as polyamide epichlorohydrin resin (for example Kymene® 557H, Hercules, Inc., Wilmington, Del., USA), polyacrylamide resins, as described for example in U.S. Pat. No. 3,556,932, commercially available polyacrylamides such as Parez® 631 NZ of the American Cyanamid Co., Stanfort, Conn., USA, ureaformaldehydes as well as melamineformaldehyde resins. Fibers which were stiffened by cross-linking connections in individual forms (i.e. the individually stiffened fibers as well as the process for their production) are for example described in U.S. Pat. Nos. 3,224,926, 3,440,135, 3,932,209 as well as in U.S. Pat. No. 4,035,147. Preferred cross-linking agents are glutaraldehyde, glyoxal, formaldehyde, glyoxalic acid, oxydisuccinic acid and citric acid. The stiffened cellulose fibers obtained by cross-linking or coating, impregnation or cross-linking can be twisted or curled, the fibers are preferably twisted and additionally curled.

Besides the above-mentioned fibrous materials the core can also include thermoplastic materials. On melting, at least a part of this thermoplastic material, typically because of the capillary gradient, penetrates between the fibers to the intersections of the fibers. These intersections become binding positions for the thermoplastic material. If the element is cooled, the thermoplastic material solidifies at these intersections, to form binding positions which hold together the matrix or the tissue of fibers in each of the respective layers. The thermoplastic materials can be in various forms, such as particles, fibers or combinations of particles and fibers. These materials can comprise a plurality of thermoplastic polymers, selected from polyolefins, such as polyethylene (for example PULPEX®) and polypropylene, polyesters, co-polyesters, polyvinylacetates, polyethylvinylacetates, polyvinylchlorides, polyvinylidenechlorides, polyacrylates, polyamides, co-polyamides, polystyrenes, polyurethanes and copolymers of the above materials, such as vinylchloride/vinylacetate and the like. For cores, predominantly materials made from cellulose, preferably fibrous, can be used as substrate.

In a further embodiment of the core this core comprises besides the substrate and the absorbent polymer further substances in the form of powders, such as for example odour binding substances such as cyclodextrins, zeolites, inorganic or organic salts or similar materials.

In one embodiment of the absorbent core the absorbent polymer is worked in a quantity within the range from about 10 to about 90, preferably from about 20 to about 80 and particularly preferably from about 40 to about 70 wt. %, based on the core. In one embodiment of the core the absorbent polymer is worked into the core as particles. Thereby the polymer particles can be homogeneously distributed in the fibrous material, they can be positioned in layered fashion between the fibrous material or the concentration of the absorbent polymer particles can have a gradient within the fibrous material. In another embodiment of the core the absorbent polymer is worked into the core as fibers.

Optionally several different absorbent polymer particles, which differ for example in the rate of absorption, in the permeability, in the retention capacity, in the absorption against pressure, the grain distribution or also in the chemical composition, can be employed simultaneously. These various polymer particles can be put already mixed together into the absorbent pad or positioned in the core with local differentiations. Such a differential positioning can occur in the direction of the thickness of the core or of the length or breadth of the core.

The core can be combined by conventional processes known to one skilled in the art, such as to one skilled in the art generally among drum-forming, by means of shaping wheels,—pockets and product forms and appropriately adapted dosing arrangements. Besides this there are modem, established process such as the so-called airlaid processes (e.g. EP 850-615, U.S. Pat. No. 4,640,810) with all forms of the dosing, depositing of the fibers and consolidation such as hydrogen bonding (e.g. DE 197 50 890), thermo-bonding, latex bonding, (e.g. EP 850 615) and hybrid bonding, the so-called wetlaid processes (e.g. WO 99/49905), carding processes, meltblown processes, spunblown processes as well as similar processes for producing superabsorbent non-wovens (in the sense of the definition of the EDANA, Brussels) also in combinations of these processes with and among usual methods for producing the cores. Further processes which could be used are the production of laminates in the broadest sense as well as of extruded and co-extruded, wet- and dry- as well as additionally reinforced structures.

In a further embodiment of the absorbent core this core comprises besides the substrate and the absorbent polymer worked into the substrate, which serve as storage layer for the body liquids, an absorbent layer which preferably serves to absorb and distribute quickly the liquid in the core. Thus the absorption layer can be arranged directly over the storage layer, it being however also possible that the absorption layer is separated from the storage layer by a preferably liquid-stable interface. This interface serves then in the first instance as support substrate for the absorption layer and the storage layer. Preferred materials for this interface are polyester spun fleeces or fleeces made from polypropylene, polyethylene or nylon.

In one embodiment of the core according to the invention the absorbent layer is free from absorbent polymer. The absorbent layer can have any suitable size and must not exceed the total length or breadth of the storage layer. The absorbent layer can for example be in the form of a strip or a patch. The total absorbent layer is preferably hydrophilic but can also have hydrophobic components. The absorbent layer can comprise a woven material, a fleece material, or another suitable type of material. The absorbent layer is preferably based on hydrophobic polyethylene-terephthalate fibers (PET fibers), chemically stiffened cellulose fibers or on mixtures of these fibers. Further suitable materials are polypropylene, polyethylene, nylon or biological fibers. If the absorbent layer comprises a fleece material, said layer can be produced by a multiplicity of different processes. These comprise wet-laying, application in an air stream, application in a melt, forming as spun fleece, carding, (this comprises thermal joining, joining with solvents or joining with the melt-spin process). The last mentioned processes (forming as spun fleece and carding) are preferred when it is desirable to align the fibers in the absorbent layer, since it is easier in such processes to align the fibers in a single direction. A particularly preferred material for the absorbent layer is a PET-spun fleece.

In the embodiment in which the composite is a diaper, the components of the diaper which are different to the absorbent polymer comprise the substrate of the composite. In a preferred embodiment the diaper comprises an above-described core. In this case the components of the diaper which are different to the core comprise the substrate of the composite. In general a composite used as a diaper comprises a water-impermeable lower layer, a water-permeable, preferably hydrophobic, upper layer and a layer comprising the absorbent polymer, which is arranged between the lower layer and the upper layer. This absorbent polymer-comprising layer is preferably a heretofore-described core. The lower layer can comprise all materials known to one skilled in the art, wherein polyethylene or polypropylene are preferred. The upper layer can likewise comprise all suitable material known to one skilled in the art, wherein polyesters, polyolefins, viscose and the like are preferred, which give a sufficiently porous layer to ensure a satisfactory liquid permeability of the upper layer. In this context reference is made to the disclosure in U.S. Pat. No. 5,061,295, U.S. Re. 26,151, U.S. Pat. No. 3,592,194, U.S. Pat. No. 3,489,148 as well as U.S. Pat. No. 3,860,003.

The invention further comprises a process for producing a composite, wherein an absorbent polymer according to the invention and a substrate and optionally a suitable additive are brought into contact with each other. The bringing into contact occurs preferably by wetlaid and airlaid processes, compression, extrusion and mixing.

In addition the invention comprises a composite which is obtainable by the above processes.

The invention is further related to chemical products, in particular foams, formed bodies, fibers, sheets, films, cables, sealant materials, liquid-absorbing hygiene articles, carriers for plant or mushroom growth regulating media or plant protection agents, additives for building materials, packing materials or soil additives, which comprise the absorbent polymer according to the invention or the above-described substrate.

The invention is additionally related to the use of absorbent polymer according to the invention or of the above described substrate in chemical products, in particular in foams, formed bodies, fibers, sheets, films, cables, sealant materials, liquid-absorbing hygiene articles, carriers for plant or mushroom growth-regulating media or plant protection agents, additives for building materials, packing materials or soil additives.

In the use as carriers for plant or mushroom growth-regulating media or plant protection agents, it is preferred that the plant or mushroom growth-regulating media or plant protection agents can be released over a time period controlled by the carrier.

The invention is now more closely illustrated by means of test methods and non-limiting examples.

Test Methods

Determination of the Drop in the AAP Value

In order to determine the drop in the AAP value determined according to ERT 442.1-99 under a pressure of 0.7 psi as a result of a mechanical treatment of the polymer particles in a ball mill the AAP value ($AAP_1$) of the polymer particles ERT 442.1-99 under a pressure of 0.7 psi was first determined. Then these polymer particles were exposed to damage via mechanical stress. To this end 10.0 g±0.1 g superabsorber were weighed into a porcelain container with 24 porcelain cylinders and sealed. Two porcelain containers were then placed on the rollers of a ball mill (Jar mill, US-Stoneware), which was set up by means of a photo-contact tachometer such that 95 rpm were reached, and the ball mill is started. The rotation time was ended by means of a stop-watch after exactly 6 minutes. Thereafter the AAP value ($AAP_2$) of the thus-treated polymer particles under a pressure of 0.7 psi was determined again. The drop in the AAP value is defined as drop in AAP value [%]=100%−(($AAP_2$/$AAP_1$)×100)

wherein respectively the average value for the $AAP_2$ or $AAP_1$ value from 20 individual measurements for the determination of the decrease in the AAP value was used.

Determination of the Absorption Time (Acquisition Time)

Figure 3:
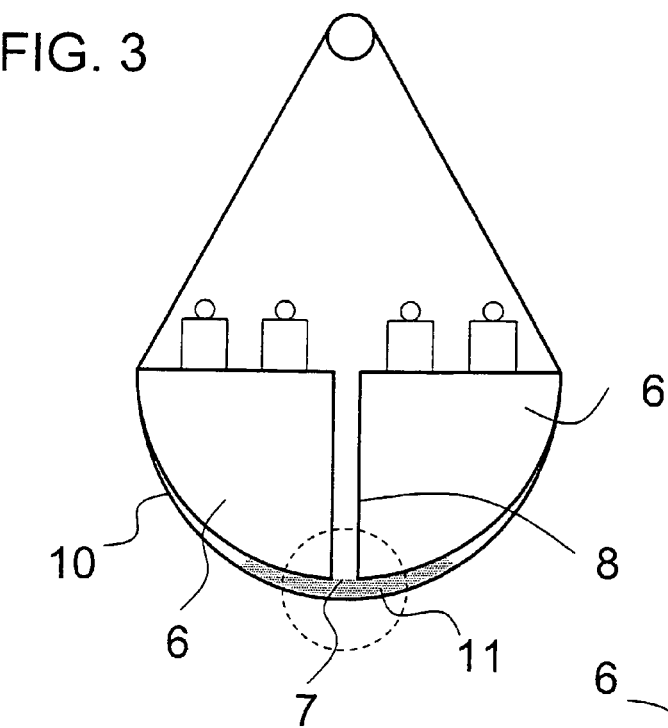
FIG. 3 illustrates the test set-up for determination of the absorption time (Acquisition Time) in cross-section.
Figure 4:
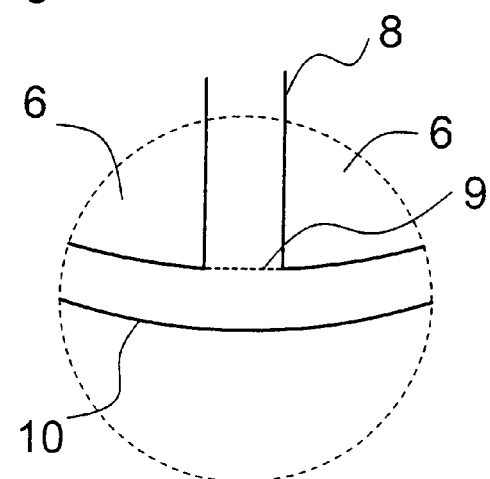
FIG. 4 illustrates a detailed view of the test set-up for determination of the absorption time (Acquisition Time).
Figure 5:
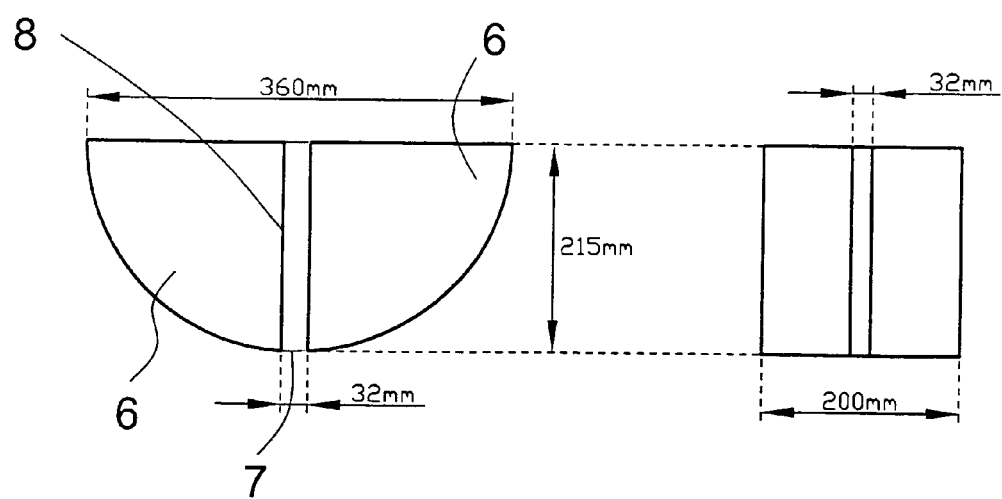
FIG. 5 illustrates a depiction of the dimensions of individual elements of the test set-up for determination of the absorption time (Acquisition Time).

In order to determine the absorption time a body-shaped test device was used, the cross-section of which is shown in FIG. 3. This consists of a body-shaped semi-cylindrical element (6) with a length of 20.5 cm with a round opening (7) and an inlet pipe (8). All surfaces of the employed parts of the test device are smooth. As can be seen from FIG. 4, which depicts a detailed view of the opening (7), this opening (7) has a sieve (9) with a mesh size of 3 to 4 mm. The element (6) was installed in a likewise essentially semicircular bowl (10). Between the element (6) and the bowl (10) in the region of the opening (7) of the inlet pipe (8) the test body (11), also named composite, was inserted. The exact dimensions of the element (6), the opening (7) as well as the inlet pipe (8), can be seen in FIG. 5. Furthermore in the measurement of the absorption time a balance with a measurement precision of 0.01 as well as weights for loading the test apparatus of one Kilo±0.5 g or pneumatic plungers, a timer, a round filter paper 90 mm for quantitative analysis from the firm Schleicher & Schuell, Type 589/1, Schwarzbrand as well as a 0.9 wt. % sodium chloride-aqua dest. test solution, which was coloured with 5 ml/l acid fuchsine stock solution. The composite to be tested was cut to a size 12 cm by 30 cm and laid in the centre of the body-shaped test apparatus between the element (6) and the bowl (10). The element (6) was loaded with 9 kg. Three times 80 g of the test solution was fed through the inlet pipe (8) via the opening (7) to the composite to be tested in intervals of 20 minutes, wherein the 20 minute interval begins with the addition of the test solution and the test solution was put all at once into the inlet pipe. The measurement of the absorption time started with the completion of the addition of the test solution and ended with the full seepage away of the test solution in the inlet pipe. The above measurement process was repeated 3 times and the respective average obtained from the thus-obtained values.

Determination of the Rewet Value

Figure 6:
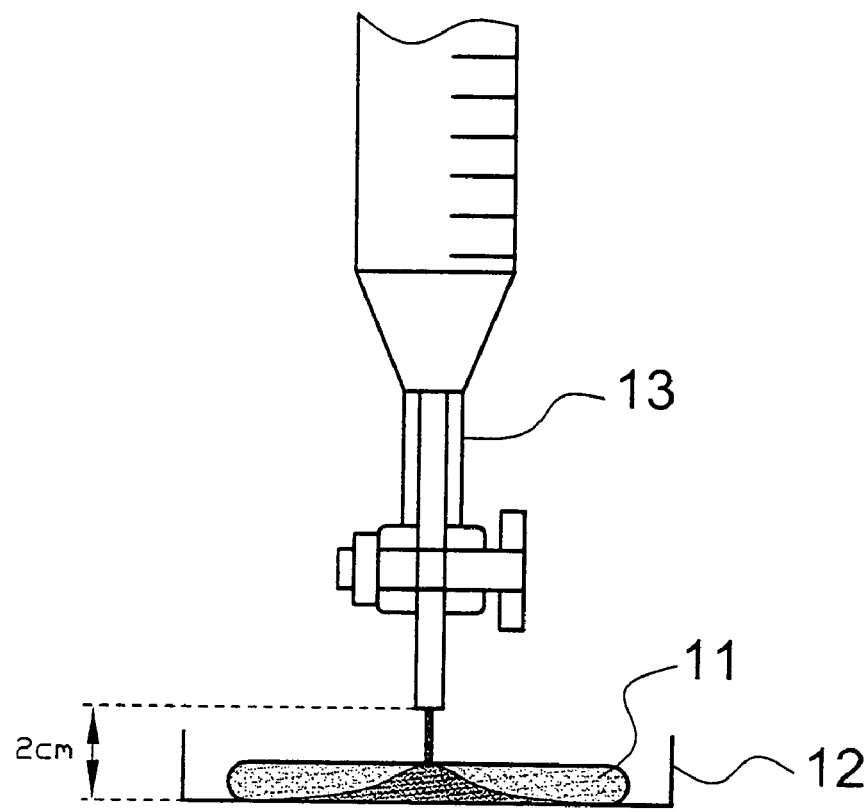
FIGS. 6 and 7 illustrate experimental set-up for determination of the rewet value.
Figure 7:
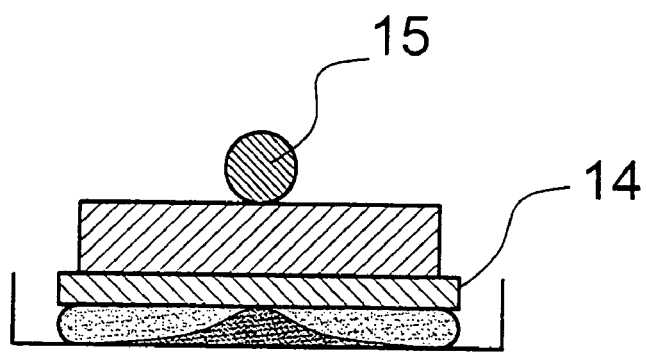

In order to determine the rewet value an experimental set-up according to FIGS. 6 and 7 was used. The composite (11) to be measured was laid in the form of a circular test item with a diameter of 9 cm, of which the weight was determined, in the middle of a petri dish (12). By means of a burette (13) 80 g of the previously described test solution were added to the centre of the test item with a flow rate of 1.8-2.0 ml/s. After stopping the addition of the test solution a likewise circular filter paper stack (14), weighing 40.0 g and with a diameter of 9 cm, of Schwarzbrand filter paper for quantitative analysis of the firm Schleicher & Schuell Type 58971, was weighed ($F_T$) and carefully laid on the top side of the test item. The filter paper stack (14) was loaded by means of weight (15) with 1,270 g to ca. 20 g/mm² for 10 minutes. After stopping the loading the filter paper stack (14) was carefully removed from the test item and weighed again ($F_F$). The rewet value is determined by $F_T$-$F_F$ [g]. The measurement is repeated 5 times and the average value obtained.

EXAMPLES

To Produce a Secondary Cross-Linked Absorbent Polymer 1.50 g Polyethyleneglycol-300-diacrylate and 1.50 g polyethyleneglycol-750-monoallyletheracrylate as cross-linkers are dissolved in 964.515 g of an aqueous solution of sodium acrylate with a degree of neutralization of 70 mol % (monomer concentration: 37.7%). The monomer solution in a plastic polymerization vessel was flushed with nitrogen for 30 minutes in order to remove dissolved oxygen. At a temperature of 4° C. the polymerization was started by successive addition of 0.3 g sodium peroxidisulfate in 10 g distilled water, 0.1 g 2,2'-azobis-2-amidinopropane-dihydrochloride in 10 g dist. water, 0.07 g 35% hydrogen peroxide solution in 10 g dist. water and 0.015 g ascorbic acid in 2 g dist. water. After the end temperature of ca. 100° C. was reached, the gel was broken up with a mincer and dried for 2 h at 150° C. in a convection oven. The dried product was coarsely ground, finely ground and the particles with sizes from 150-850 μm sieved out for further transformation (powder A).

Comparison Example 1

50 g Powder A was mixed with vigorous stirring with a solution of 0.15 g aluminium sulfate 18-hydrate and 0.15 g water and then with a solution of 0.3 g ethylene carbonate and 0.3 g water and finally kept in a convection oven at 170° C. for 90 minutes (powder B). Powder B is characterized by the properties listed in Table 1.

TABLE 1

| Property of powder B | Unit | Measurement result |
| --- | --- | --- |
| CRC | g/g | 28.7 |
| AAP (0.7 psi) | g/g | 21.6 |
| Decrease in AAP (0.7 psi) | % | 24 |

Example 1

200 g of the secondary cross-linked absorbent polymer (powder B) was put into an rotation jar of a rapidly rotating MTI mixer (MTI mixing technology, Industrieanlagen GmbH, 322758 Detmold: type LM 1.5/5; year of construction 1995) which rotates (volume ca. 1 l) with a speed of the mixing aggregate of 1000 rpm. 4 ml Deionized water was then measured in by syringe. After ca. 5 to 15 seconds the liquid and the absorbent polymer are homogeneously mixed. After a waiting time of 15 minutes (maturation) a second agitation event was carried out with a Krups-Drei-Mixer 3000 at level 1 (slowest revolution speed) over 5 minutes, hereby those particles still adhered to each other were separated from each other and a free-flowing, clump-free material obtained (powder C). Powder C is characterized by the properties listed in Table 2.

TABLE 2

| Property of powder C | Unit | Measurement result |
|---|---|---|
| CRC | g/g | 28.8 |
| AAP (0.7 psi) | g/g | 21.2 |
| Decrease in AAP (0.7 psi) | % | 4.8 |

Preparation of Composites for Test Items

The composites were formed by means of a mixture of 50 wt. % of an absorbent polymer (powder B or C), based on the composite, and 47.5 wt. % cellulose fibers Stora Fluff EF semitreated from Stora-Enzo AB Sweden, as well as 2.5 wt. % of a two-component fiber of respectively 50 wt. % polypropylene (PP) or polyethylene (PE) with a PP core and a PE coat from the firm Fibervision A/S Denmark by an airlaid process with a M&J machine (width 40 cm, operating width 36 cm, operational set-up: band speed 2 m/min, fluff drawing-in at hammer mill 3.6 m/min, polymer dosage 400 g/min, two-component fiber discharged in 10 g portions 0.7 times/min), wherein the absorbent polymer was added homogeneously. Composites with a basis weight of 870 g/m² including tissue (1 layer, 18 g/m²), with a density of 0.16 g/cm³ were used as test items for the following tests. The results of the test carried out are summarized in Table 3.

TABLE 3

| Sample | Absorption time after first wetting[s] | Absorption time after second wetting[s] | Absorption time after third wetting[s] | Rewet [g] |
|---|---|---|---|---|
| Powder B | 53 | 253 | 475 | 12.55 |
| Powder C | 45 | 197 | 399 | 10.48 |

| List of Reference Characters | |
|---|---|
| 1 | polymer particles |
| 1', 1" | stuck together polymer particles |
| 2 | liquid |
| 3 | wetted polymer particles |
| 4 | speed direction of the polymer particle 1 or of the polymer particles 1, 1' or 1" |
| 5 | adhesion layer between two polymer particles 1 |
| 6 | element |
| 7 | opening |
| 8 | inlet pipe |
| 9 | sieve |
| 10 | bowl |
| 11 | composite |
| 12 | petri dish |
| 13 | burette |
| 14 | filter paper |
| 15 | weight |

The invention claimed is:

1. A process for producing an absorbent polymer composition comprising the steps of:
   a first mixing event, wherein a plurality of absorbent polymer particles are mixed with a liquid in a mixer; and
   a second mixing event, wherein the liquid is distributed within the polymer particles;
   wherein the polymer particles in the first mixing event are mixed with a first mixing speed, and the polymer particles in the second mixing event are stirred with a lower speed than in the first mixing event; and
   wherein the first mixing event is a continuous mixing process
   wherein in the first mixing event the polymer particles are back-mixed in such a way that a flow of the new polymer particles entering in the mixer is overlaid by a flow of polymer particles already present in the mixer and opposed to this flow, wherein the ratio of the opposed flow to the flow of newly entering polymer particles averages about 5 to about 50% by wt.

2. The process according to claim 1 wherein before the first mixing event the absorbent polymer particles have been secondary cross-linked in the surface portion and have been brought into contact with a composition comprising an $Al^{3+}$ ion before the secondary cross-linking.

3. The process according to claim 1 wherein the average speed of the polymer particles in the first mixing event amounts to between about 8 and about 80 m/sec.

4. The process according to claim 1 wherein the Froude number in the first mixing event amounts to between about 1 and about 50.

5. The process according to claim 1 wherein a back-mixing from about 10% to about 30% occurs.

6. The process according to claim 1 wherein the average residence time of the first mixing event amounts to between about 5 and about 200 sec.

7. The process according to claim 1 wherein the static pressure build up during the first mixing event amounts to less than about 0.1 bar.

8. The process according to claim 1 wherein water or aqueous solution is added as liquid.

9. The process according to claim 8, wherein the liquid comprises additives.

10. The process according to claim 1, wherein the polymer particles are based on:
   ($\alpha$1) about 0.1 to about 99.999 wt.% polymerized, ethylenically unsaturated, acidic group-containing monomers containing a protonated or a quaternary nitrogen, or mixtures thereof,
   ($\alpha$2) 0 to about 70 wt.% of polymerized, ethylenically unsaturated monomers which can be co-polymerized with ($\alpha$1),
   ($\alpha$3) about 0.001 to about 10 wt.% of one or more cross-linkers,
   ($\alpha$4) 0 to about 30 wt.% of water soluble polymers, as well as
   ($\alpha$5) 0 to about 20 wt.% of one or more additives, wherein the sum of the component weights ($\alpha$1) to ($\alpha$5) amounts to 100 wt.%.

11. The process according to claim 1 wherein the polymer particles have at least one of the following properties:
   (A) the maximum absorption of 0.9 wt.% NaCl solution is within a range from at least about 10 to about 1000 g/g SAP granulate,
   (B) the part extractable with 0.9 wt.% aqueous NaCl solution amounts to less than about 30 wt.%, based on the SAP granulate,
   (C) the bulk density is within a range from about 300 to about 1000 g l,
   (D) the pH value for 1 g of the SAP granulate in 1 l water is within a range from about 4 to about 10,
   (E) the CRC value is within a range from about 10 to about 100 g/g, (F) the AAP value under a pressure of 0.7 psi is within a range from about 10 to about 60 g/g, (G) the AAP value under a pressure of 0.3 psi is within a range from about 10 to about 100 g/g.

12. A process for producing a composite, wherein the absorbent polymer composition made according to claim 1 and a substrate and optionally an additive are brought into contact with each other.

13. The process according to claim 3 wherein the speed of the polymer particles in the second mixing process amounts to under about 3 m/sec.

14. The process according to claim 1 wherein the Froude number in the second mixing event amounts to between about 0.001 and about 1.

* * * * *